US007553132B2

(12) United States Patent
Jiang et al.

(10) Patent No.: US 7,553,132 B2
(45) Date of Patent: Jun. 30, 2009

(54) MICRO DEVICE INCORPORATING PROGRAMMABLE ELEMENT

(75) Inventors: Hongrui Jiang, Madison, WI (US); David J. Beebe, Madison, WI (US); Abhishek K. Agarwal, Madison, WI (US); Francisco J. Atencia-Fernandez, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 539 days.

(21) Appl. No.: 11/133,901

(22) Filed: May 20, 2005

(65) Prior Publication Data

US 2006/0002804 A1 Jan. 5, 2006

Related U.S. Application Data

(60) Provisional application No. 60/572,983, filed on May 20, 2004.

(51) Int. Cl.
*F04B 49/00* (2006.01)
*C12M 1/38* (2006.01)
*F01D 15/12* (2006.01)
*F16D 27/00* (2006.01)

(52) U.S. Cl. ................ 417/214; 435/286.5; 435/286.7; 415/123; 192/21.5

(58) Field of Classification Search ............ 416/169 R, 416/169 A; 415/123; 192/21.5, 58.1, 82 T, 192/58.63; 188/266; 417/214; 435/286.5, 435/286.7

See application file for complete search history.

(56) References Cited

U.S. PATENT DOCUMENTS

| | | | | |
|---|---|---|---|---|
| 4,350,305 | A * | 9/1982 | van Hoorn | 241/46.017 |
| 5,409,034 | A * | 4/1995 | Ostertag et al. | 137/499 |
| 5,815,181 | A * | 9/1998 | Kashino et al. | 347/65 |
| 6,488,872 | B1 * | 12/2002 | Beebe et al. | 264/31 |
| 7,064,472 | B2 * | 6/2006 | Pelrine et al. | 310/324 |
| 7,296,592 | B2 * | 11/2007 | Rehm et al. | 137/528 |
| 2002/0194909 | A1 * | 12/2002 | Hasselbrink et al. | 73/253 |
| 2003/0019520 | A1 * | 1/2003 | Beebe et al. | 137/93 |
| 2005/0175478 | A1 * | 8/2005 | Marr et al. | 417/410.1 |

OTHER PUBLICATIONS

Atencia J., and Beebe, D. "An Oscillating Ferromagnetic Micropump Utilizing Centrifugal Force." from the 7th International Conference on Miniaturized Chemical and Biochemical Analysis Systems, Oct. 5-9, 2003.*

Lu, L. et al. "A Magnetic Microstirrer and Array for Microfluidic Mixing." Journal of Microelectromechanical Systems, vol. 11, No. 5, Oct. 2002.*

"Physics and Applications of Microfluidics In Biology," Annu. Rev. Biomed. Eng. 2002, 4:261-86 by David J. Beebe, Glennys A. Mensing and Glenn M. Walker.

* cited by examiner

*Primary Examiner*—Charles G Freay
(74) *Attorney, Agent, or Firm*—Boyle Fredrickson, S.C.

(57) ABSTRACT

A micro device is provided that includes a body defining a chamber for receiving fluid. A rotational element is disposed in the chamber for acting on the fluid. The rotational element is rotatable about an axis in response to a rotating magnetic field. The micro device further includes a clutch mechanism having a first disengaged configuration and a second engaged configuration wherein the clutch mechanism engages the rotational element and prevents rotation of the same.

30 Claims, 6 Drawing Sheets

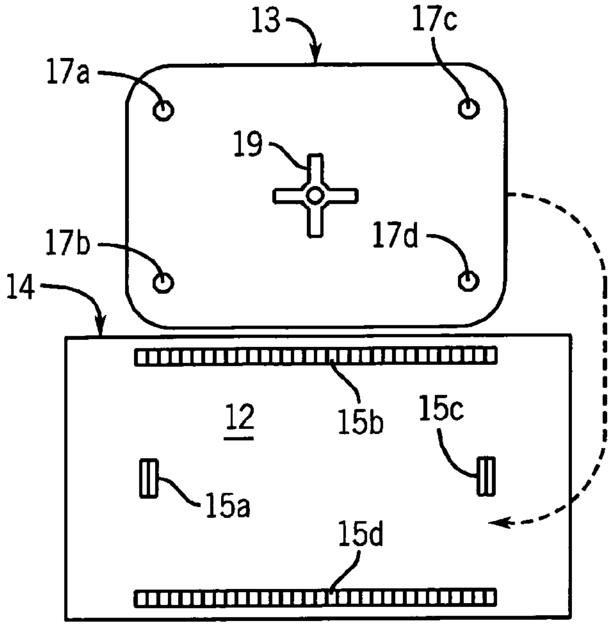
FIG. 1
FIG. 2
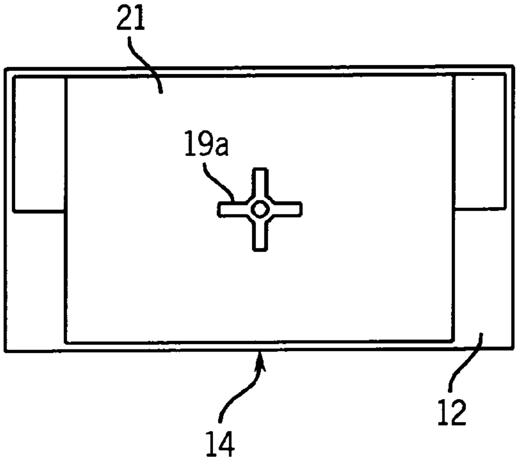
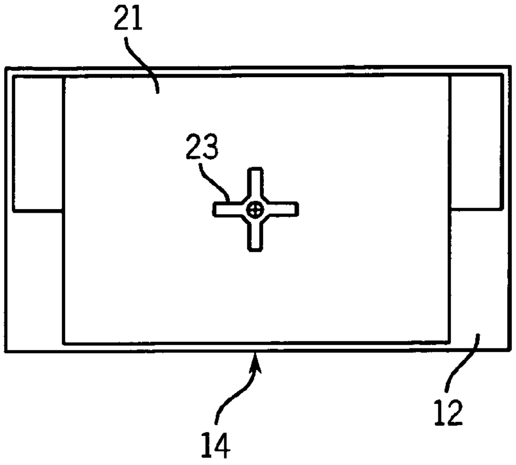
FIG. 3

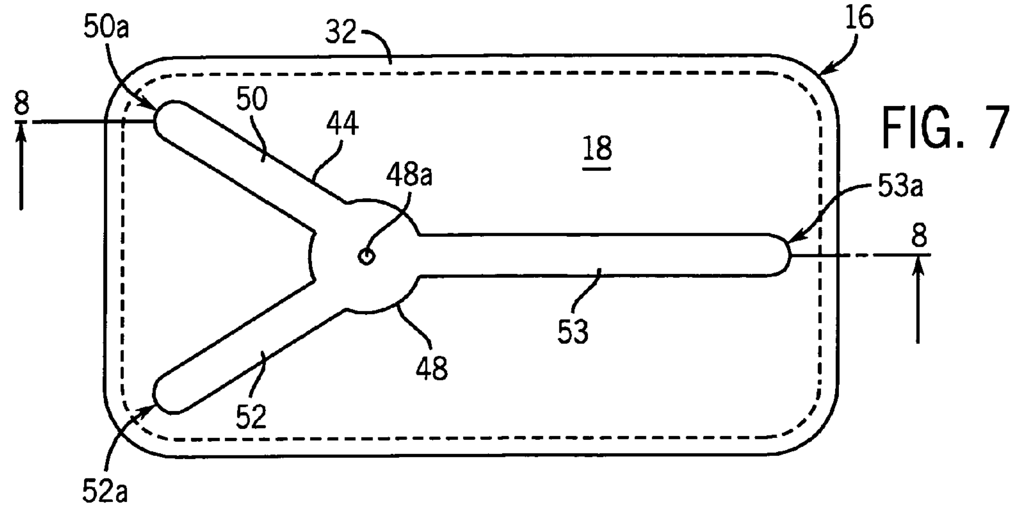
FIG. 7
FIG. 8
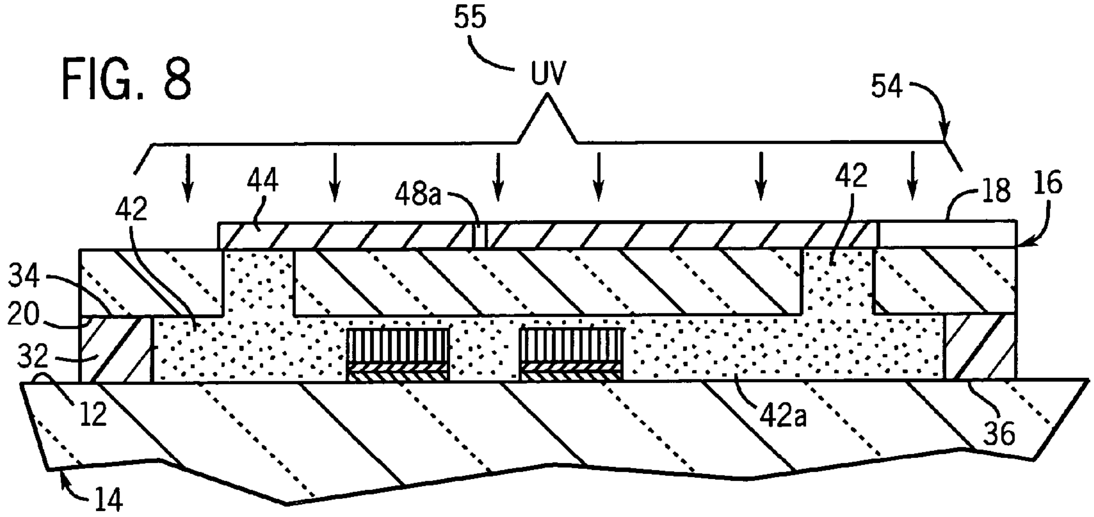
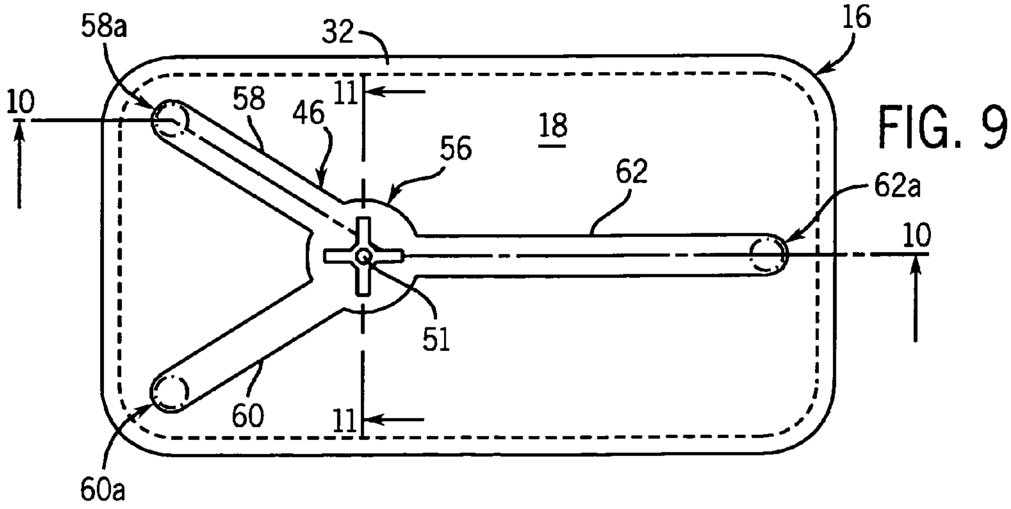
FIG. 9

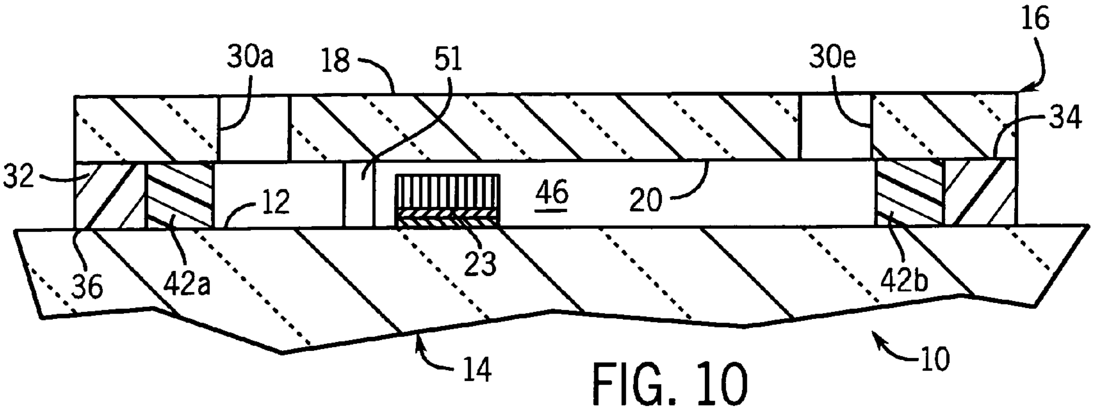
FIG. 10
FIG. 11
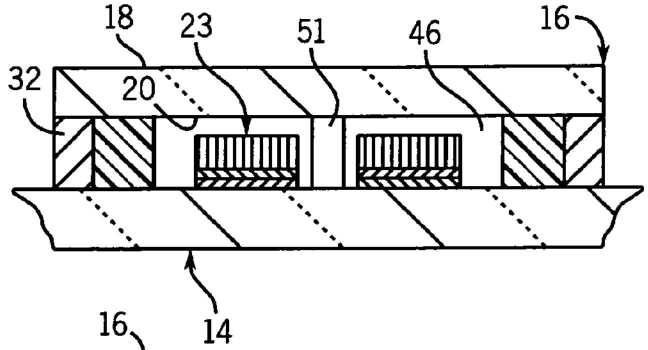
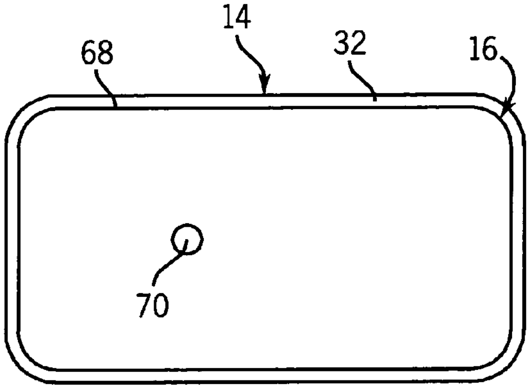
FIG. 12
FIG. 13
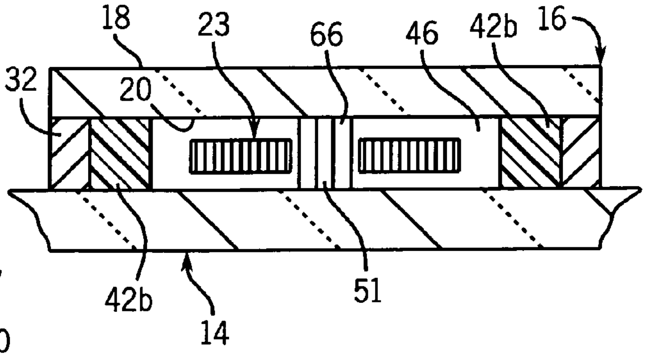
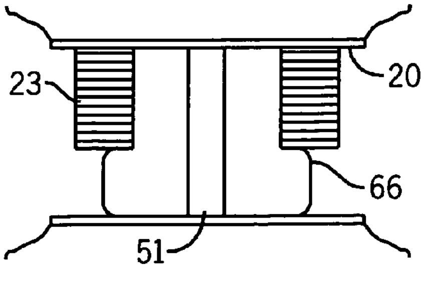
FIG. 13a

MICRO DEVICE INCORPORATING PROGRAMMABLE ELEMENT

CROSS-REFERENCE TO RELATED APPLICATION

This application claims the benefit of U.S. Provisional Application Ser. No. 60/572,983, filed May 20, 2004.

REFERENCE TO GOVERNMENT GRANT

This invention was made with United States government support awarded by the following agencies: DOD ARPA F30602-00-2-0570. The United States has certain rights in this invention.

FIELD OF THE INVENTION

This invention relates generally to microsystems, and in particular, to a micro device incorporating a programmable rotational element for acting on a fluid flowing therepast.

BACKGROUND AND SUMMARY OF THE INVENTION

As is known, Microsystems have emerged as a useful tool in such areas as electronics, research and clinical medicine. Microsystems are considered to be any device or unit made up of a number of microengineered and/or micromachined components, such as miniature pumps and valves. In an attempt to develop Microsystems that perform more complex functions, ongoing research is being conducted in the area of microelectromechanical systems (MEMS). Due to various innovations in the integrated circuit industry (e.g., micromachining), the development of microsystems has progressed rapidly. For example, various microsystems which incorporate microengineered and/or micromachined components such as sensors, actuators, valves and the like are now widely used in academia. These microsystems are designed for various applications, including microfluidics and drug delivery.

Further expansion of the uses for microsystems has been limited due to the difficulty and expense of fabrication. While silicon-based Microsystems have proven well suited to optical and physical sensing applications, the use of silicon-based devices in other applications is not straightforward. Silicon-based approaches typically rely on actuation methods (electrostatic, thermal, electromagnetic) that are not suitable for direct interface with liquid and organic systems. In addition, the integration of microscale valves and other microscale components into micro devices has proven problematic. Often, the manufacturing process that provides a useful microscale valve is vastly different from the manufacturing process that provides a useful microscale pump or sensor. Hence, different device components necessarily require different materials for construction and different types of manufacturing steps. As a result, the integrating of several microengineered components into a single micro device is both time consuming and expensive.

In order to overcome the limitations of prior MEMS technology, polymer-based fabrication techniques have been developed. During polymer-based fabrication, liquid-phase photopolymerization is utilized to allow for the rapid creation of microcomponents. As a result, photosensitive polymers can be patterned within a micro device without the additional necessity of a clean-room environment. Further, liquid-phase photopolymerization is a low-temperature process (<100 degrees Celsius) and allows the fabricator to construct a desired microcomponent at a designated area on a substrate.

Hence, it is highly desirable to provide a method of fabricating a micro device that leverages the advantages of both silicon-based Microsystems with polymer-based fabrication techniques.

Therefore, it is a primary object and feature of the present invention to provide a micro device that incorporates a programmable element that functions without on-chip wiring or electricity.

It is a further object and feature of the present invention to provide a micro device that is simple and inexpensive to manufacture.

It is a still further object and feature of the present invention to provide a micro device that may be customized to a particular application without undue additional expense.

In accordance with the present invention, a micro device is provided that includes a body defining a chamber. The chamber has an input and an output for accommodating the flow of fluid therebetween. The micro device includes a moveable element disposed in the chamber and a clutch mechanism engageable with the moveable element for controlling the movement thereof.

The clutch mechanism has a first configuration wherein the moveable element is fixed in position and a second configuration wherein the moveable element is free move along a path. The clutch mechanism includes a polymeric material having a volume responsive to the value of an environmental property such as the pH or temperature of the fluid. The material has a first volume in response to the environmental property having a first value and a second volume in response to the property having a second value.

The moveable element includes a central hub that may have a blade extending radially therefrom and an opening therein for receiving the polymeric material. The opening is defined by an inner hub surface that is engaged by the polymeric material when the polymeric material has the second volume. As a result, the polymeric material prevents movement of the moveable element.

In a first embodiment, the blade has a terminal end radially spaced from and interconnected to the central hub by a generally arcuate edge. Alternatively, the blade may include first and second edges extending radially from the central hub and diverging from each other. It is contemplated for an alternate embodiment of the moveable element to include a radially outer edge having a plurality of teeth circumferentially spaced thereabout.

In accordance with a further aspect of the present invention, a micro device is provided that includes a body defining a chamber. The chamber has an input and an output for accommodating the flow of fluid therebetween. A rotational element is disposed in the chamber. The rotation element includes a central hub and is rotatable about an axis. A clutch mechanism is engageable with the rotational element in response to an environmental property. The clutch mechanism controls rotation of the rotational element.

The central hub of the rotational element has an opening therethrough for receiving a post disposed in the chamber. The clutch mechanism includes a polymeric material that extends about the post and that has a volume responsive to the value of the environmental property, such as the pH or temperature of the fluid. The polymeric material has a first volume in response to the property having a first value and a second volume in response to the property having a second value. The opening through the central hub of the rotational element is defined by an inner hub surface. In its second volume, the polymeric material engages the inner hub surface and prevents rotation of the rotational element.

In a first embodiment, the blade has a terminal end radially spaced from and interconnected to the central hub by a generally arcuate edge. Alternatively, the blade may include first and second edges extending radially from the central hub and diverging from each other. An alternate embodiment of the rotational element includes a radially outer edge having a plurality of teeth circumferentially spaced thereabout.

In accordance with a still further aspect of the present invention, a micro device is provided. The micro device includes a body defining a chamber for receiving fluid. A moveable element is disposed in the chamber and is moveable along a predetermined path in response to an external stimulus. The micro device further includes a clutch mechanism having a first disengaged configuration and a second engaged configuration wherein the clutch mechanism engages the moveable element.

The clutch mechanism is movable between the disengaged configuration and the engaged configuration in response to an environmental property, such as the pH or temperature of the fluid. The moveable element includes a central hub having an opening therethrough for receiving a post disposed in the chamber. The clutch mechanism includes polymeric material extending about the post. The polymeric material has a volume responsive to the value of the environmental property. The polymeric material is spaced from the moveable element with the clutch mechanism in the first disengaged configuration and the polymeric material engages the moveable element with the clutch mechanism in the second engaged configuration.

The body defines a first input channel having an output communicating with the chamber and an output channel having an input communicating with the chamber. In a first embodiment, the body may define a second input channel having an output communicating with the chamber. Alternatively, the body may define a feedback channel having an input communicating with the output channel downstream of the chamber and an output communicating with the input channel upstream of the chamber.

BRIEF DESCRIPTION OF THE DRAWINGS

The drawings furnished herewith illustrate a preferred methodology of the present invention in which the above advantages and features are clearly disclosed as well as others which will be readily understood from the following description of the illustrated embodiment.

In the drawings:

FIG. 1 is a schematic view of a first step in fabricating a micro device in accordance with the present invention;

FIG. 2 is a schematic view of a second step in fabricating the micro device of the present invention;

FIG. 3 is a schematic view of a third step in fabricating the micro device of the present invention;

FIG. 7 is a top plan view of the micro device of FIG. 5 having an optical mask affixed to the upper surface thereof;

FIG. 8 is a cross-sectional view of the micro device of the present invention taken along line 8-8 of FIG. 7 showing a fifth step in the method of the present invention wherein a cavity within the micro device has polymerizable material injected therein;

FIG. 9 is a top plan view of the micro device of the present invention during the fabrication process;

FIG. 10 is a cross-sectional view of the micro device of the present invention taken along line 10-10 of FIG. 9;

FIG. 11 is a cross-sectional view of the micro device of the present invention taken along line 11-11 of FIG. 9;

FIG. 12 is a top plan view of the micro device of FIG. 9 having a second optical mask affixed to the upper surface thereof;

FIG. 13 is a cross-sectional view, similar to FIG. 11, of the completed micro device of the present invention;

Figure 15:
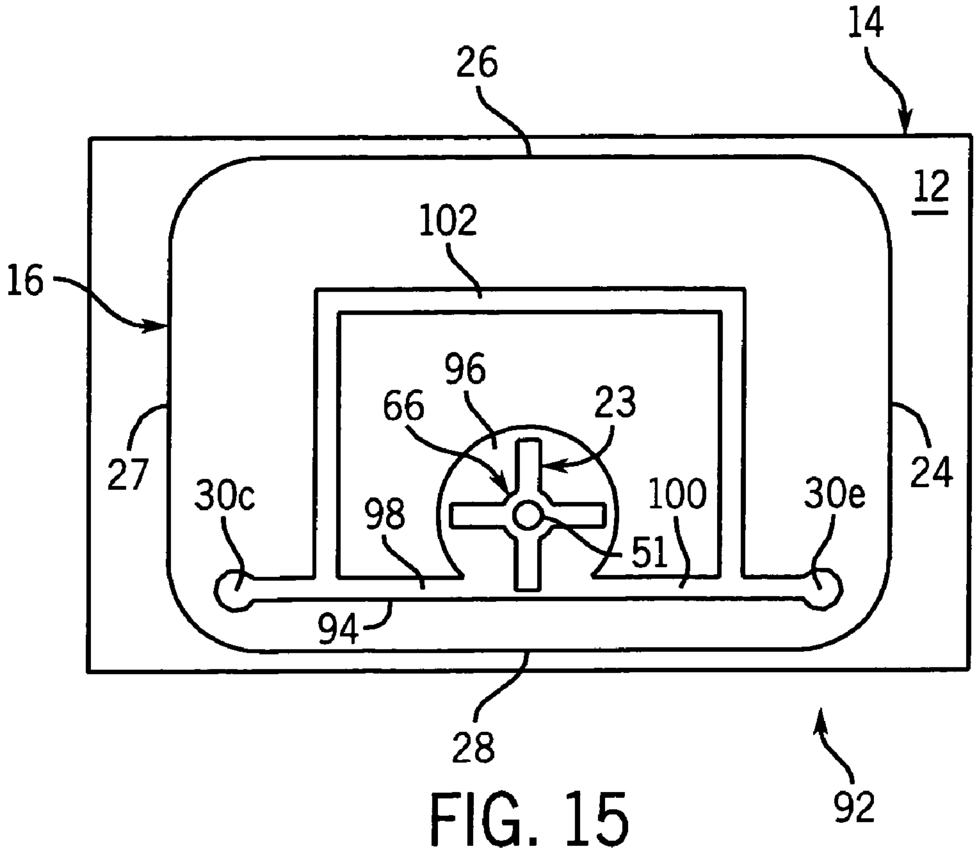

FIG. **13*a*** is a cross-sectional view of the completed micro device of the present invention with the hydrogel clutch mechanism thereof in an expanded configuration;

FIG. **14*a*** is a top plan view of a first embodiment of a rotational element for the micro device of the present invention;

FIG. **14*b*** is a top plan view of a second embodiment of a rotational element for the micro device of the present invention;

FIG. **14*c*** is a top plan view of a third embodiment of a rotational element for the micro device of the present invention;

FIG. **14*d*** is a top plan view of a fourth embodiment of a rotational element for the micro device of the present invention;

FIG. **14*e* is a top plan view of a fifth embodiment of a rotational element for the micro device of the present invention; and FIG. 15** is a schematic, top plan view of an alternate embodiment of a micro device in accordance with the present invention.

DETAILED DESCRIPTION OF THE DRAWINGS

Referring to FIGS. 13 and 15, a micro device fabricated in accordance with a methodology as hereinafter described is generally designated by the reference numeral 10. Referring to FIG. 1, in order to fabricate micro device 10, optical mask 13 is positioned on upper surface 12 of microscope slide 14. It is contemplated for slide 14 to be formed from glass, however, other substrates, such as a silicon wafer or print circuited board may be used without deviating from the scope of the present invention. Upper surface 12 of slide 14 is coated with a bottom layer of titanium (Ti) of approximately 0.05 micrometers, an intermediate layer of copper (Cu) of approximately 0.35 micrometers, and a top layer of Ti of 0.05 micrometers. The bottom layer of Ti serves to promote adhesion of the coating to slide 14. The top layer of Ti prevents oxidation of the intermediate layer of Cu.

Optical mask 13 is spaced from upper surface 12 of slide 14 by a plurality of pieces **15*a*-15*d* of double sided adhesive tape so as to define a cavity therebetween. Mask 13 includes a plurality of fill holes 17*a*-17*d* to allow the cavity to be filled with a polymerizable material, e.g. a pre-polymer mixture of poly-isobornylacrylate, tetraethylene glycol dimethacrylate, and 2,2-dimethoxy-2-phenylacetophenone, and pattern 19 thereon corresponding to the desired shape to be transferred to the polymerizable material, as hereinafter described. Ultraviolet light generated by UV source 55, FIG. 8, is directed towards optical mask 13 at an angle generally perpendicular thereto. As is known, the polymerizable material within the cavity between optical mask 13 and upper surface 12 of slide 14 polymerizes and solidifies when exposed to ultraviolet light 54. It can be appreciated that pattern 19 of optical mask 13** shields a portion of the polymerizable material from the ultraviolet light such that the portion not exposed to the ultraviolet light does not polymerize and remains in a fluidic state.

Figure 4:
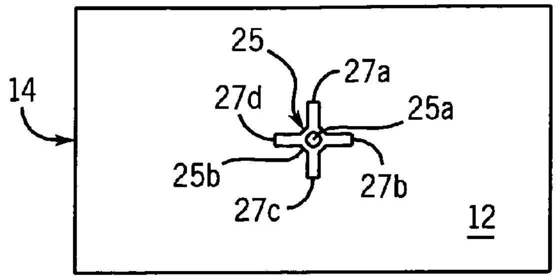
FIG. 4 is a top plan view of the micro device of the present invention during the fabrication process.

Referring to FIGS. 2-3, optical mask 13 is removed and the fluidic portion of the polymerizable material is flushed from cavity 19*a* in polymerized material 21 utilizing ethanol. Thereafter, the portion of the top layer of Ti communicating with cavity 19*a* is removed by placing slide 14 in a bath of $HF:H_2O=1:10$, thereby exposing the underlying intermediate layer of Cu. The exposed portion of the intermediate layer of Cu is rinsed with water and placed in a nickel sulfamate bath. Nickel (Ni) is electroplated onto the exposed portion of the intermediate layer of Cu to form rotational element 23. Polymerized material 21 is removed from slide 14 by soaking slide 14 in methanol for several hours. In addition, the portions of the Ti/Cu/Ti layers on upper surface 12 of slide 14 outside of rotational element 23 are selectively removed utilizing HAC: $H_2O_2:H_2O=1:1:10$. As best seen in FIG. 4, rotational element 23 includes central hub 25 having an inner surface 25*a* defining a central aperture therethrough and a radially outer surface 25*b*. A plurality of circumferentially spaced mixing blades 27*a*-27*d* extending from outer surface 25*b* of central hub 25, for reasons hereinafter described.

Figure 5:
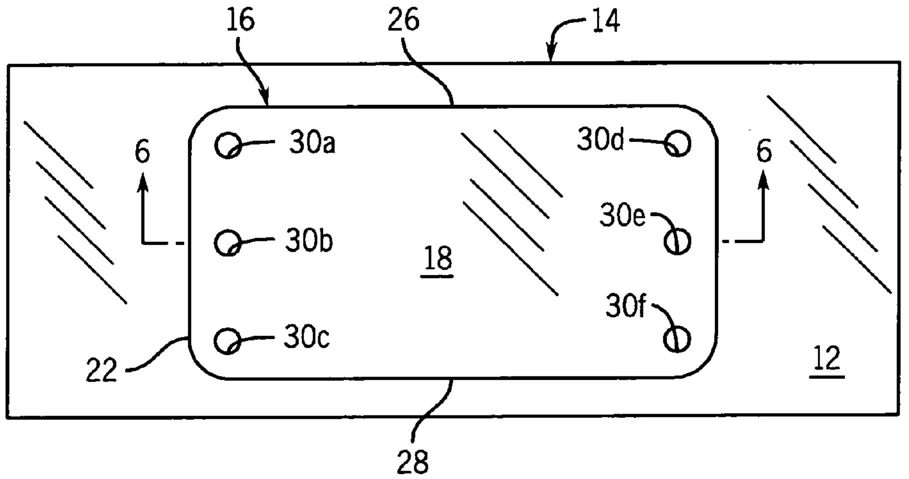
FIG. 5 is a schematic, top plan view of a fourth step in fabricating the micro device of the present invention.
Figure 6:
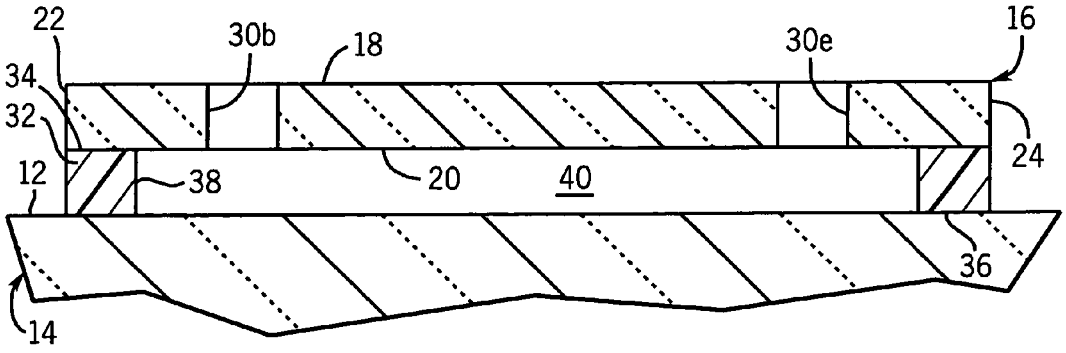
FIG. 6 is a cross-sectional view of the micro device of the present invention taken along line 6-6 of FIG. 5.

Referring to FIGS. 5-6, cartridge 16 is formed from a polycarbonate material and includes upper and lower surfaces 18 and 20, respectively, interconnected by first and second ends 22 and 24, respectively, and first and second sides 26 and 28, respectively. A plurality of fill holes 30*a*-30*f* extend through cartridge 16 and communicate with upper and lower surfaces 18 and 20, respectively, thereof.

Gasket 32 includes an upper surface 34 affixed to lower surface 20 of cartridge 16 adjacent the outer periphery thereof. Lower surface 36 of gasket 32 is affixed to upper surface 12 of microscope slide 14. As assembled, inner surface 38 of gasket 32, lower surface 20 of first layer 16 and upper surface 12 of microscope slide 14 define a cavity 40 for receiving polymerizable material 42 therein, FIG. 8. The material is injected into cavity 40 through any one of the openings 30*a*-30*f* through the cartridge 16.

Referring to FIG.7, optical mask 44 is affixed to upper surface 18 of first layer 16. It is intended that optical mask 44 correspond to the shape of a channel network 46 to be formed in cavity 40, FIG. 9, as hereinafter described. By way of example, optical mask 44 is generally Y-shaped and includes a generally circular central portion 48 having aperture 48*a* extending therethrough that overlaps a portion of the aperture though central hub 25 of rotational element 23. First and second legs 50 and 52, respectively, diverge from central portion 48 and terminate at ends 50*a* and 52*a* that overlap openings 30*a* and 30*c*, respectively, through cartridge 16. In addition, optical mask 44 includes third leg 53 extending therefrom and terminating at end 53*a* overlapping opening 30*e* of cartridge 16.

As best seen in FIG. 8, ultraviolet light generally designated by the reference numbers 54 is generated by UV source 55, and is directed towards micro device 10 at an angle generally perpendicular to upper surface 18 of cartridge 16. As is known, the polymerizable material 42 polymerizes and solidifies when exposed to ultraviolet light 54. It can be appreciated that optical mask 44 shields a first portion 42*a* of the polymerizable material 42 from ultraviolet light 54. As a result, second portion 42*b* of material 42, which is exposed to ultraviolet light 54, polymerizes and solidifies. On the other hand, first portion 42*a* of material 42, which is not exposed to ultraviolet light 54, does not polymerize and remains in a fluidic state.

Referring to FIGS. 9-11, after polymerization of second portion 42*b* of material 42 by ultraviolet light 54, optical mask 44 is removed from upper surface 18 of cartridge 16. In addition, the non-polymerized portion 42*a* of the material is flushed from channel network 46 and openings 30*a*, 30*c* and 30*e* in first layer 16 using ethanol. It can be appreciated that channel network 46 has a generally Y-shape that corresponds to the shape of optical mask 44 and includes post 51 projecting vertically from upper surface 12 of slide 14 into channel network 46 through the aperture in central hub 25 of rotational element 23. Channel network 46 includes central chamber 56 housing rotational element 23. First and second legs 58 and 60, respectively, extending from central chamber 56 and diverge from each other. Terminal end 58*a* of leg 58 of channel network 46 communicates with opening 30*a* through cartridge 16. Terminal end 60*a* of second leg 60 of channel network 46 communicates with opening 30*c* through cartridge. Channel network 46 further includes third leg 62 extending from central chamber 56 and terminating at terminal end 62*a* that communicates with opening 30*e* through cartridge 16.

After formation of channel network 46, hydrogel 66 is injected into channel network 46 through any one of the openings 30*a*, 30*c* or 30*d* through the cartridge 16 and optical mask 68 is affixed to upper surface 18 of first layer 16, FIG. 12. It is intended that optical mask 68 include opening 70 therethrough corresponding to a desired pattern for the hydrogel 66 about post 51, for reasons hereinafter described. Ultraviolet light is directed towards micro device 10 at an angle generally perpendicular to upper surface 18 of cartridge 16 such that a gel matrix is formed about post 51 that changes its volume configuration depending on its surrounding environment. For example, hydrogel 66 may expand and contract in response to stimuli such as changes in temperature, light, electric fields or pH levels of the environment within central chamber 56 of channel network 46. However, it can be appreciated that hydogel 66 may be responsive to other environmental parameters without deviating from the scope of the present invention. Thereafter, rotational element 23 is released from upper surface 12 of slide 14 by flowing Ti and/or Cu etching solutions into central chamber 56 so as to remove the portions of the Ti and Cu layers from between slide 14 and rotational element 23, FIG. 13.

In operation, it is contemplated to expose micro device 10 to an external stimulus such as an electric field or a rotating magnetic field so as to cause rotational element 23 to rotate in a user desired direction about post 51. First and second fluids may be introduced into channel network 46 at openings 30*a* and 30*c* in cartridge 16 so as to flow towards central chamber 56. As the first and second fluids flow into central chamber 56, mixing blades 27*a*-27*d* engage the first and second fluids causing such fluids to mix. Thereafter, due to the flow rates and pressures of the first and second fluids, the mixed fluid is urged into third leg 62 in channel network 46 toward opening 30*e* in cartridge 16. In response to a change in a predetermined environmental parameter, the volume of hydrogel 66 may increase to such point that hydrogel 66 engages inner surface 25*a* of central hub 25 of rotational element 23 thereby slowing the rate of rotation of rotational element 23 about post 51. It can be appreciated that if the predetermined environmental parameter reaches a predetermined level or value, hydrogel 66 will expand to such a volume as to prevent the further rotation of rotational element 23 despite the presence of the rotating magnetic field. It is contemplated for hydrogel 66 to expand to such a volume as to overlap portions of the upper and lower surfaces of rotational element 23. Once the level of the predetermined environmental parameter drops below the predetermined level, the volume of hydrogel 66 will shrink thereby allowing rotational element 23 to, once again, rotate about post 51.

Alternatively, in response to the predetermined environmental parameter reaching a predetermined level or value, hydrogel 66 may expand into a mushroom cap shaped configuration, FIG. 13*a*. In the mushroom cap shaped configuration, hydrogel 66 exerts both a lateral force against inner surface 25*a* of central hub 25 of rotational element 23 and a downward force on the upper surface of rotational element 23 thereby causing rotational element 23 to stop rotating. Once the level of the predetermined environmental parameter drops below the predetermined level, the volume of hydrogel 66 will shrink, as heretofore described, thereby allowing rotational element 23 to, once again, rotate about post 51.

Figure 14A:
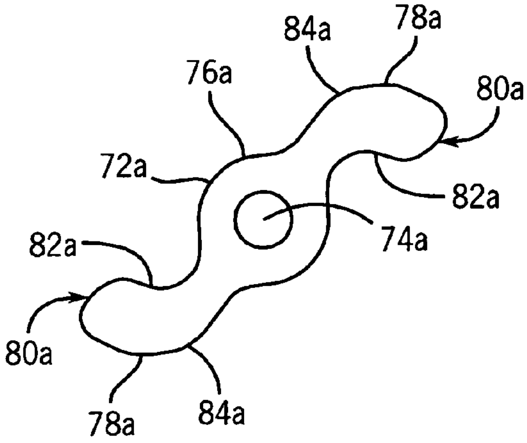

The efficiency of the mixing process within central chamber 56 is dependant on a variety of variables, including the dimensions of mixing blades 27*a*-27*d*, the diameter of central chamber 56, the flow rates and pressure of the first and second fluids flowing into central chamber 56 and the diameters of first, second, and third legs 58, 60 and 62, respectively, of channel network 46. As such, alternate rotational elements 70*a*-70*d* are contemplated as being within the scope of the present invention, FIGS. 14*a*-14*d*. Referring to FIG. 14*a*, alternate rotational element 70*a* includes central hub 72*a* having inner surface 74*a* defining a central aperture therethrough for receiving the post 51 and hydrogel 66 combination, as heretofore described, and radially outer surface 76*a*. First and second circumferentially spaced mixing blades 78*a* extend from outer surface 76*a* of central hub 72*a*. Each mixing blade 78*a* is defined by terminal end 80*a* interconnected to outer surface 76*a* by generally arcuate edges 82*a* and 84*a*.

Figure 14C:
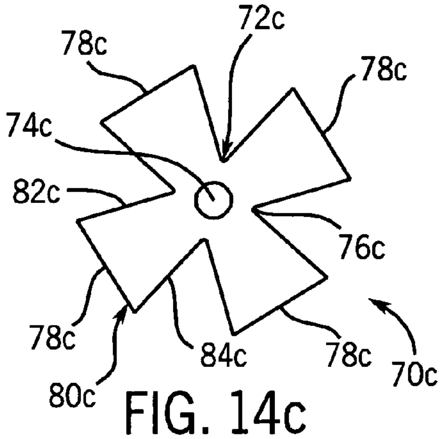
Figure 14B:
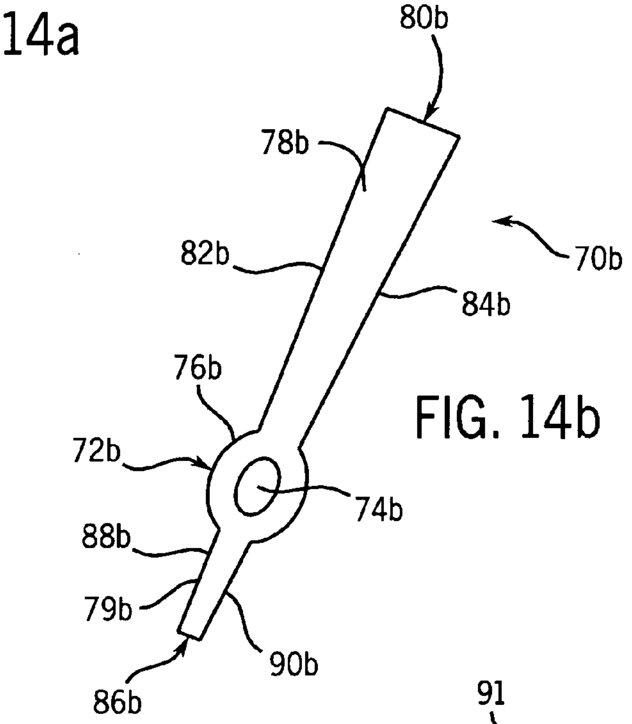

Referring to FIG. 14*b*, alternate rotational element 70*b* includes central hub 72*b* having inner surface 74*b* defining a central aperture therethrough for receiving the post 51 and hydrogel 66 combination, as heretofore described, and radially outer surface 76*b*. First and second circumferentially spaced mixing blades 78*b* and 79*b*, respectively, extend from outer surface 76*a* of central hub 72*a*. Mixing blade 78*b* is defined by terminal end 80*b* interconnected to outer surface 76*b* by first and second diverging edges 82*b* and 84*b*, respectively. Mixing blade 79*b* is defined by terminal end 86*b* interconnected to outer surface 76*b* by first and second generally parallel edges 88*b* and 90*b*, respectively.

Referring to FIG. 14*c*, alternate rotational element 70*c* includes central hub 72*c* having inner surface 74*c* defining a central aperture therethrough for receiving the post 51 and hydrogel 66 combination, as heretofore described, and radially outer surface 76*c*. Circumferentially spaced mixing blades 78*c* extend radially from outer surface 76*c* of central hub 72*c*. Each mixing blade 78*c* is defined by terminal end 80*c* interconnected to outer surface 76*c* by first and second diverging edges 82*c* and 84*c*, respectively.

Figure 14D:
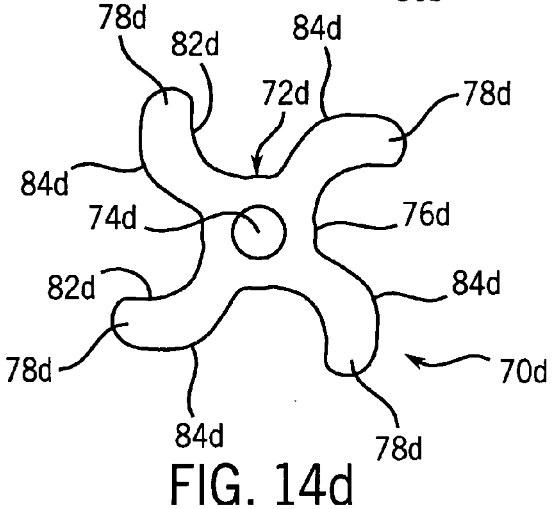

Referring to FIG. 14*d*, alternate rotational element 70*d* includes central hub 72*d* having inner surface 74*d* defining a central aperture therethrough for receiving the post 51 and hydrogel 66 combination, as heretofore described, and radially outer surface 76*d*. A plurality of circumferentially spaced mixing blades 78*d* extend from outer surface 76*d* of central hub 72*d*. Each mixing blade 78*d* is defined by terminal end 80*d* interconnected to outer surface 76*d* by generally arcuate edges 82*d* and 84*d*.

Figure 14E:
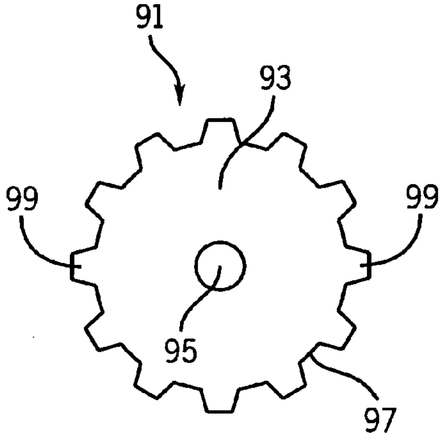

It can be appreciated that channel network 46 may be fabricated to have different configurations within micro device 10 by simply varying the configurations of optical mask 44. In addition, it is contemplated as being within the scope of the present invention for micro device 10 to perform additional tasks beyond mixing. As such, rotational element 23 may take the form of a moveable element that moves along a linear path, arc-like path, or even an arbitrary part in response to a stimulus provided on micro device 10. Alternatively, as best seen in FIG. 14*e*, rotational element 91 may take the form of a gear, adapted for driving a secondary gear or a device. Rotational element 91 includes central hub 93 having inner surface 95 defining a central aperture therethrough for receiving the post 51 and hydrogel 66 combination, as heretofore described, and radially outer surface 97. A plurality of circumferentially spaced teeth 99 extends from outer surface 97 of central hub 93. Teeth 99 of rotational element 91 are adapted to engage teeth on an adjacent gear or to drive an adjacent device in a conventional manner.

Referring to FIG. 15, an alternate embodiment of a micro device in accordance with the present invention is generally designated by the reference numeral 92. Micro device 92 is fabricated on slide 14 as heretofore described with respect to micro device 10 such that the polymerized portion 42*b* of polymerizable material 42 defines channel network 94 therein. Channel network 94 includes central chamber 96 having the post 51 and hydrogel 66 combination projecting vertically from upper surface 12 of slide 14 through the aperture in central hub 25 of rotational element 23. Channel network 94 further includes input leg 98 having an input communicating with opening 30*c* in cartridge 16 and an output communicating with central chamber 96, as well as, output leg 100 having an output communicating with opening 30*e* in cartridge 16 and an input communicating with central chamber 96. Feedback channel 102 has an input communicating with output leg 100 and an output communicating with input leg 98.

In operation, micro device 92 is exposed to an external stimulus such as an electric field or a rotating magnetic field so as to cause rotational element 23 to rotate in a user desired direction about the post 51 and hydrogel 66 combination. A first fluid is introduced into channel network 94 at opening 30*c* in cartridge 16 and flows toward central chamber 96 through input leg 98. As the first fluid flows into central chamber 96, blades 27*a*-27*d* engage the first fluid, thereby pumping such fluid into output leg 100. A portion of the first fluid returns to input leg 98 through feedback channel 102. In response to a change in a predetermined environmental parameters, the volume of hydrogel 66 increase to such point that hydrogel 66 engages inner surface 25*a* of central hub 25 of rotational element 23 thereby slowing the rate of rotation of rotational element 23 about post 51 and slowing the pumping of the first fluid into output leg 100. It can be appreciated that if the predetermined environmental parameter reaches a predetermined level, hydrogel 66 will expand to such a volume as to prevent the further rotation of rotational element 23. As heretofore described, hydrogel 66 may expand to such a volume as to overlap to upper surface of rotational element 23 or portions of the upper and lower surfaces of rotational element 23. Once the level of the predetermined environmental parameter drops below the predetermined level, the volume of hydrogel 66 will shrink thereby allowing rotational element 23 to, once again, rotate about post 51 and pump the first fluid into output leg 100.

As described, the method of fabrication provided herein may be used as a stand-alone process or to append an existing procedure. Unlike conventional lithography that requires the spinning and/or casting of photosensitive materials on entire substrates, liquid-phase photopolymerization can occur at designated areas on a substrate. The process can also be appended to MEMS structures that have been previously released. Since the process described herein is liquid based, topography in not a significant concern. In addition, the ability to control component operation via local fluid parameters expands control scheme possibilities while in situ processing simplifies fabrication and eliminates the need for assembly. Further, it can be appreciated that the method of fabricating micro device 10 described herein is merely exemplary and that micro device 10 may be fabricated in other manners without deviating from the scope of the present invention.

Various modes of carrying out the invention are contemplated as being within the scope of the following claims particularly pointing out and distinctly claiming the subject matter that is regarded as the invention.

We claim:

1. A micro device including a body that defines a chamber, the chamber having an input and an output for accommodating the flow of fluid therebetween, comprising:

a moveable element disposed in the chamber, the moveable clement including an inner surface defining an opening in the moveable element; and a clutch mechanism engageable with the moveable element for controlling the movement thereof, the clutch mechanism including an expandable polymeric material having a volume responsive to the value of a predetermined environmental property such that the material has a first volume in response to the environmental property having a first value and a second volume in response to the environmental property having a second value;

wherein:

the polymeric material extends through the opening in the element;

the polymeric material engages the inner surface of the element and prevents movement of the element with the polymeric material having the first volume; and the polymeric material disengages from the inner surface of the element with the polymeric material having the second volume so as to allow the element to move with respect to the polymeric material.

2. The micro device of claim 1 wherein the polymeric material has a mushroom cap shape in the first volume.

3. The micro device of claim 1 wherein the moveable element includes a hub having at least one blade extending radially therefrom.

4. The micro device of claim 3 wherein the hub includes the opening therein for receiving the polymeric material.

5. The micro device of claim 3 wherein the blade has a terminal end radially spaced from and interconnected to the hub by a generally arcuate edge.

6. The micro device of claim 3 wherein the blade includes first and second edges extending radially from the hub and diverging from each other.

7. The micro device of claim 1 wherein the moveable element includes a radially outer edge having a plurality of teeth circumferentially spaced thereabout.

8. The micro device of claim 1 wherein the environmental property is pH of the fluid.

9. The micro device of claim 1 wherein the environmental property is temperature of the fluid.

10. A micro device, comprising:

a body defining a chamber, the chamber having an input and an output for accommodating the flow of fluid therebetween;

a rotational element disposed in the chamber and including a hub having an inner surface defining a central opening through the rotational member, the rotational element being rotatable about an axis; and a clutch mechanism extending through the central opening in the hub of the rotational element and being movable between a first disengaged configuration wherein the clutch mechanism is disengaged from the inner surface of the hub of the rotational clement and a second engaged configuration wherein the clutch mechanism engages the inner surface of the hub of the rotational element in response to an environmental property of the fluid, the clutch mechanism controlling rotation of the rotational element.

11. The micro device of claim 10 wherein the micro device further comprises a post disposed in the chamber and extending through the central opening in the hub.

12. The micro device of claim 11 wherein the clutch mechanism includes polymeric material extending about the post and having a volume responsive to the value of the environmental property, the polymeric material having a first volume in response to the environmental property having a first value and a second volume in response to the environmental property having a second value.

13. The micro device of claim 12 wherein the polymeric material of the second volume engages the inner hub surface and prevents rotation of the rotational element.

14. The micro device of claim 13 wherein the rotational element includes an upper surface and wherein polymeric material of the second volume engages the upper surface of the rotational element to prevent rotation of the rotational element.

15. The micro device of claim 11 wherein the rotational clement includes a blade extending radially from the hub.

16. The micro device of claim 15 wherein the blade has a terminal end radially spaced from and interconnected to the hub by a generally arcuate edge.

17. The micro device of claim 15 wherein the blade includes first and second edges extending radially from the hub and diverging from each other.

18. The micro device of claim 15 wherein the rotational element includes a radially outer edge having a plurality of teeth circumferentially spaced thereabout.

19. The micro device of claim 11 wherein the environmental property is pH of the fluid.

20. The micro device of claim 11 wherein the environmental property is temperature of the fluid.

21. The micro device of claim 11 wherein the body includes a second input to the chamber.

22. A micro device, comprising:

a body defining a chamber for receiving fluid;

a moveable element disposed in the chamber and being moveable along a path in response to a predetermined external stimulus, the moveable element including a hub having an inner surface defining an opening through the moveable element; and a clutch mechanism extending through the opening in the moveable element and having a first disengaged configuration wherein the clutch mechanism is disengaged from the moveable element and a second engaged configuration wherein the clutch mechanism engages the moveable element and prevents movement of the moveable element along the path, the clutch mechanism being movable between the disengaged configuration and the engaged configuration in response to an environmental property of the fluid.

23. The micro device of claim 22 wherein the environmental property is pH of the fluid.

24. The micro device of claim 22 wherein the environmental property is temperature of the fluid.

25. The micro device of claim 22 further comprising a post disposed in the chamber and extending through the opening in the hub of the moveable element.

26. The micro device of claim 25 wherein the clutch mechanism includes polymeric material extending about the post, the polymeric material having a volume responsive to the value of the environmental property.

27. The micro device of claim 26 wherein the polymeric material is spaced from the moveable element with the clutch mechanism in the first disengaged configuration and wherein the polymeric material engages the moveable element with the clutch mechanism in the second engaged configuration.

28. The micro device of claim 22 wherein the body defines a first input channel having an output communicating with the chamber and an output channel having an input communication with the chamber.

29. The micro device of claim 28 wherein the body defines a second input channel having an output communicating with the chamber.

30. The micro device of claim 28 wherein the body defines a feedback channel having an input communicating with the output channel downstream of the chamber and an output communicating with the input channel upstream of the chamber.

* * * * *